United States Patent [19]
Bylsma et al.

[11] Patent Number: 4,777,146
[45] Date of Patent: Oct. 11, 1988

[54] FABRICATION PROCESS INVOLVING SEMI-INSULATING MATERIAL

[75] Inventors: Richard B. Bylsma, Red Bank; Alastair M. Glass, Rumson, both of N.J.

[73] Assignee: American Telephone and Telegraph Company, AT&T Bell Laboratories, Murray Hill, N.J.

[21] Appl. No.: 42,397

[22] Filed: Feb. 24, 1987

[51] Int. Cl.⁴ .................. H01L 21/265; G01R 1/04
[52] U.S. Cl. ............................. 437/008; 250/492.3; 324/158 R
[58] Field of Search .................. 437/8; 250/492.3; 324/158

[56] References Cited

U.S. PATENT DOCUMENTS

| | | | |
|---|---|---|---|
| 4,332,833 | 6/1982 | Aspnes et al. | 29/574 |
| 4,408,884 | 10/1983 | Kleinknecht et al. | 356/355 |
| 4,456,879 | 6/1984 | Kleinknecht | 324/158 D |
| 4,496,900 | 1/1985 | Di Stefano et al. | 324/24 |
| 4,575,922 | 3/1986 | Nemiroff | 29/574 |
| 4,640,002 | 2/1987 | Phillips et al. | 29/574 |

OTHER PUBLICATIONS

D. S. Chemla, D. J. Eilenberger, and P. W. Smith, "Degenerate Four-Wave Mixing in Room-Temperature GaAs/GaAlAs Multiple Quantum Well Structures", *Applied Physics Letters*, vol. 42, No. 11, Jun. 1, 1983, pp. 925-927.

J. F. Nye, *Physical Properties of Crystals*, Oxford University Press, London, England, 1957.

J. I. Pankove, *Optical Processes in Semiconductors*, Dover Publications, Inc., New York, NY, 1971, pp. 62-67.

T. E. Van Eck, L. M. Walpita, W. S. C. Chang, and H. H. Wieder, "Franz-Keldysh Electrorefraction and Electroabsorption in Bulk InP and GaAs", *Applied Physics Letters*, vol. 48, No. 7, Feb. 17, 1986, pp. 451-453.

R. J. Coller, C. B. Burckhardt and Lawrence H. Lin, *Optical Holography*, Academic Press, New York, NY, 1971.

F. T. S. Yu, *Introduction to Diffraction, Information Processing, and Holography*, The Massachusetts Institute of Technology, Boston, MA, 1973.

A. M. Glass, "The Photorefractive Effect", *Optical Engineering*, vol. 17, No. 5, Sep.-Oct. 1978, pp. 470-479.

P. Dobrilla and J. S. Blakemore, "Optical Mapping of Residual Stress in Czochralski Grown GaAs", *Applied Physics Letters*, vol. 48, No. 19, May 12, 1986, pp. 1303-1305.

G. C. Valley and M. B. Klein, "Optimal Properties of Photorefractive Materials for Optical Data Processing", *Optical Engineering*, vol. 22, No. 6, Nov./Dec. 1983, pp. 704-711.

S. M. Sze, *Physics of Semiconductor Devices*, John Wiley & Sons, New York, NY, 1981.

*Primary Examiner*—Upendra Roy
*Attorney, Agent, or Firm*—Bruce S. Schneider

[57] ABSTRACT

Semi-insulating wafers such as semi-insulating gallium arsenide wafers are commonly utilized in the fabrication of semiconductor devices, e.g., lasers and optical detectors. The quality of wafer electrical properties is determined before device processing by an optical technique. In this technique a refractive index change is induced with incident light and the rate of decay of this refractive index change upon change of incident light intensity is monitored with a second beam. The rate of decay is directly related to electrical properties such as resistivity. Subsequent processing is then based on this measurement.

21 Claims, 4 Drawing Sheets

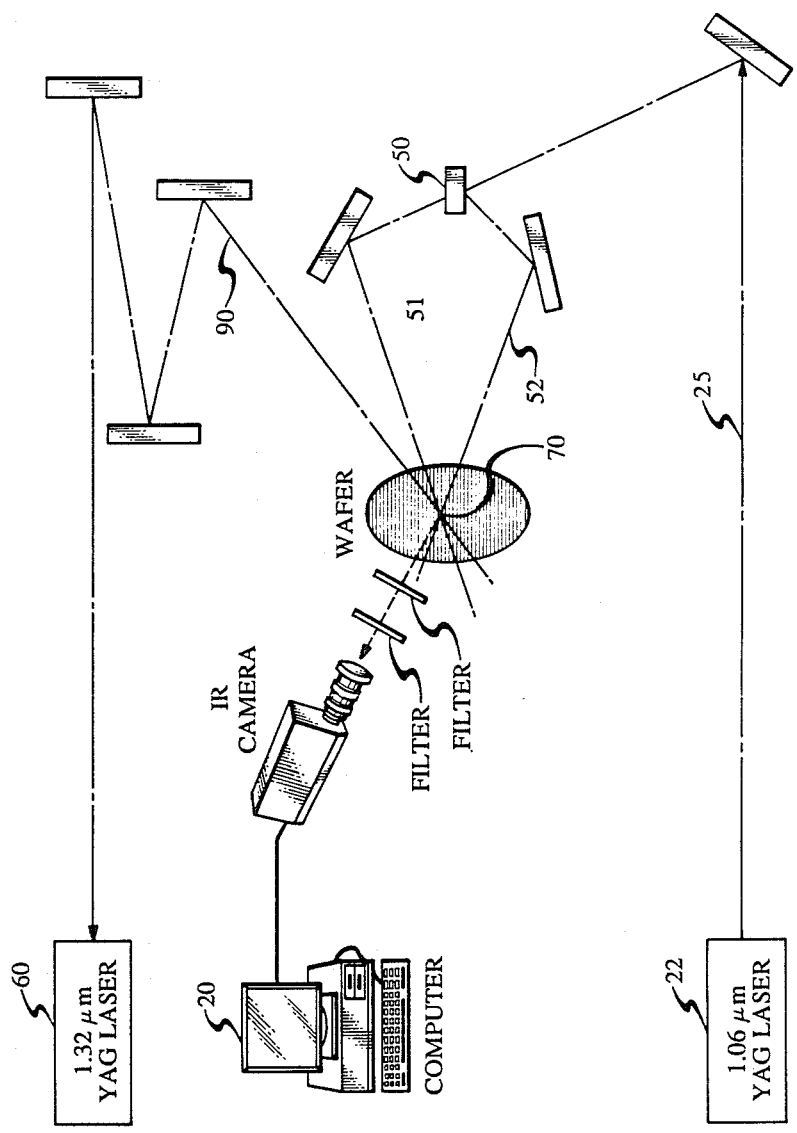

FABRICATION PROCESS INVOLVING SEMI-INSULATING MATERIAL

BACKGROUND OF THE INVENTION

1. Field of the Invention

This invention relates to compound semiconductor device procesing and, in particular, to compound semiconductor device processing involving a semi-insulating wafer.

2. Art Background

Most compound semiconductor electronic device fabrication is accomplished by using a semi-insulating wafer as a starting, mechanically stable body. For example, in the fabrication of gallium arsenide integrated circuits (IC) the various device layers necessary to produce the IC are either built upon and/or implanted in a semi-insulating gallium arsenide substrate and then the processed wafer is cleaved or cut into a plurality of devices. The semi-insulating wafers are produced by introducing deep level traps. For example, indium phosphide is made semi-insulating by doping with either iron or titanium and gallium arsenide is made semi-insulating either by doping with chromium or by a suitable adjustment of the stoichiometry.

Since the processing of a wafer into a plurality of devices is an expensive procedure, substantial cost is avoided by ensuring that the semi-insulating wafer is of an acceptable material before costs are incurred in subsequent processing. For example, to produce suitable devices, a semi-insulating wafer should have uniform electrical properties and, in particular, resistivity uniformity. An electrical property is generally sufficiently uniform for most devices if it varies across the surface of a wafer, e.g., a 2 inch wafer no more than a factor of 2 preferably no more than 10 percent. Poorer uniformity leads to excessive variation of device characteristics over a wafer. If the resistivity is less than $10^6$ ohm-cm then devices formed in this low resistivity area typically exhibit excessive leakage current.

Presently, the electrical properties of a wafer are checked by depositing electrodes on the wafer, applying a field to effect the desired measurement, and subsequently removing the electrodes. The application of the electrodes, however, for many semiconductor materials such as gallium arsenide often unacceptably diminishes device production speed. The deposition of electrodes also increases the possibility of surface contamination. Additionally, the accuracy of this measurement in determining crystal quality is somewhat suspect. For example, the interface between the electrode and the wafer introduces measured resistivity not actually present in the wafer.

An optical absorption measurement which does not require electrode deposition has also been made to determine the concentration of deep level traps present in the water. (See, P. Dobrilla and J. S. Blakemore, *Applied Physics Letters*, 48, 1303 (1986).) The measured trap level is then correlated with resistivity. This correlation from optical to electrical properties is, nevertheless, approximate at best. Thus, a reliable, non-intrusive method for testing the resistivity of semi-insulating wafers has not been reported.

SUMMARY OF THE INVENTION

A non-intrusive optical method for accurately determining electrical properties such as uniformity of resistivity in semi-insulating wafers derived from compound semiconductor material, e.g., III-V and II-VI compound semiconductor material, is advantageously employed in the manufacture of wafers and device fabricated from these wafers. In this procedure the wafer is subjected to a first beam of electromagnetic radiation. This beam is chosen to produce a refractive index change in the wafer, i.e., a refractive index differing from the unilluminated level. The magnitude of refractive index change for a given intensity of incident light is a much more sensitive measure of absorption spatial variation and thus trap levels than the optical transmission measurements presently being made. Even more significantly, by terminating the beam and monitoring the rate of decay of the induced refractive index change with another incident beam of electromagnetic radiation further precise information is gained. In particular, the exponential decay rate described by G. C. Valley and M. B. Klein, *Optical Engineering*, 22, 704 (1983) is directly related to the product of the resistivity and the dielectric constant. (Extensive listings for dielectric constants are found, for example, in *Physics of Semiconductor Device*, S. M. Sze, p. 848, John Wiley & Sons, New York, 1981.) The spatial resolution of this technique is also quite good. Thus, the spatial uniformity of resistivity is easily determined. Additionally, by attenuating or increasing the incident beam, a measurement of photoconductivity is obtained as described in G. C. Valley and M. B. Klein, *Optical Engineering*, 22, 704 (1983).

If the measured properties are acceptable for the device yield ultimately desired, the wafer is employed. Alternatively, a representative wafer from a batch of wafers is measured by this optical technique and the batch is either employed or discarded depending upon the results of the optical measurement.

Since an optical procedure is utilized, the difficulties associated with measurements using electrodes is avoided. The measurement is easily automated, relatively simple to perform, and yields an efficient, accurate determination of critical electrical parameters for semi-insulating wafers. Sources of inaccuracies such as non-ohmic electrode contacts are avoided, and thus, bulk electrical properties are measured.

BRIEF DESCRIPTION OF THE DRAWING

FIGS. 1 and 4 are illustrative of various apparatuses suitable for practicing the invention;

DETAILED DESCRIPTION

In accordance with the invention, a wafer having a material that undergoes a refractive index change when subjected to an electric field is optically inspected for suitability. (Materials that undergo such change include materials having zinc blende crystal structure, e.g., III-V and II-VI based semiconductor materials.) If the wafer is suitable, it is then employed, e.g., sold or processed into a plurality of devices. Alternatively, a representative wafer or wafers from a plurality of wafers is chosen. These representative wafers are then optically inspected and if the optical inspection yields appropriate results, subsequent device processing is performed or the wafer is sold to a device fabricator.

The optical system utilized in the invention includes a means for providing electromagnetic radiation (inducing radiation) that induces a refractive index change in the semi-insulating wafer, and a means for providing electromagnetic radiation (monitoring radiation) that is suitable for monitoring the decay rate of the refractive index after the intensity of the inducing electromagnetic radiation is reduced. (The monitoring beam is also employable for monitoring the refractive index change upon illumination as well as change induced by an attenuation or increase in the magnitude of the inducing beam.) In the measurement for resistivity, the inducing radiation is terminated and monitoring light is employed of a distinct wavelength that preferably itself does not induce a significant change in refractive index. In the measurement of photoconductivity, the intensity of the inducing radiation is lowered or increased and either this beam of altered intensity is employed or a second beam is employed as the monitoring light. It is thus possible depending on the measurement being made that the inducing electromagnetic radiation and the monitoring electromagnetic radiation either emanate from the same light source, e.g., laser and/or are identical except for intensity.

Figure 2:
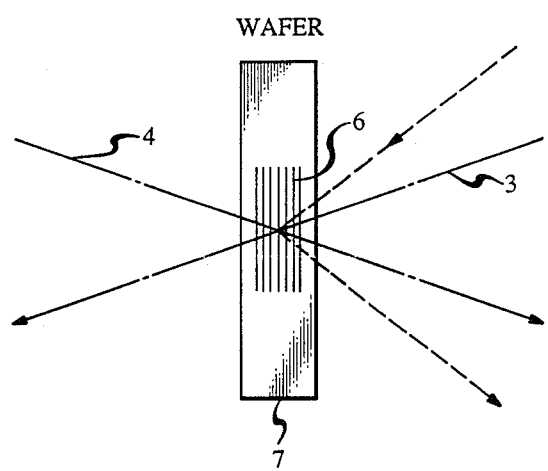
FIG. 2 is illustrative of a configuration for inducing and detecting a diffraction grating profile.

The spatial configuration of the induced refractive change in the wafer is not critical. For example, in an advantageous embodiment the refractive index change forms a diffraction grating. This formation of a diffraction grating, 6, in the wafer 7 is accomplished through the interaction of two inducing light beams as shown by 3 and 4 in FIG. 2, e.g., through holography. Alternatively, a region of uniformly increased refractive index is produced. (See, e.g., *Optical Holography*, Collier, Academic Press, New York (1971), and *Introduction to Diffraction Information Processing in Holography*, F. T. S. Yu, M.I.T. Press, Massachusetts (1973), for descriptions of how diffraction grating and regions of uniform refractive index are produced and detected. Also, see "The Photorefractive Effect", *Optical Engineering*, A. M. Glass, Vol. 17, p. 470 (1978).) In any embodiment, however, the wafer should be oriented so that the inducing radiation creates an index variation by the electro-optic effect. (See, for instance, Nye, *Physical Properties of Crystals*, Clarendon, Oxford (1957) for a table of electro-optic tensors and the appropriate orientation for a variety of materials.)

Figure 1:
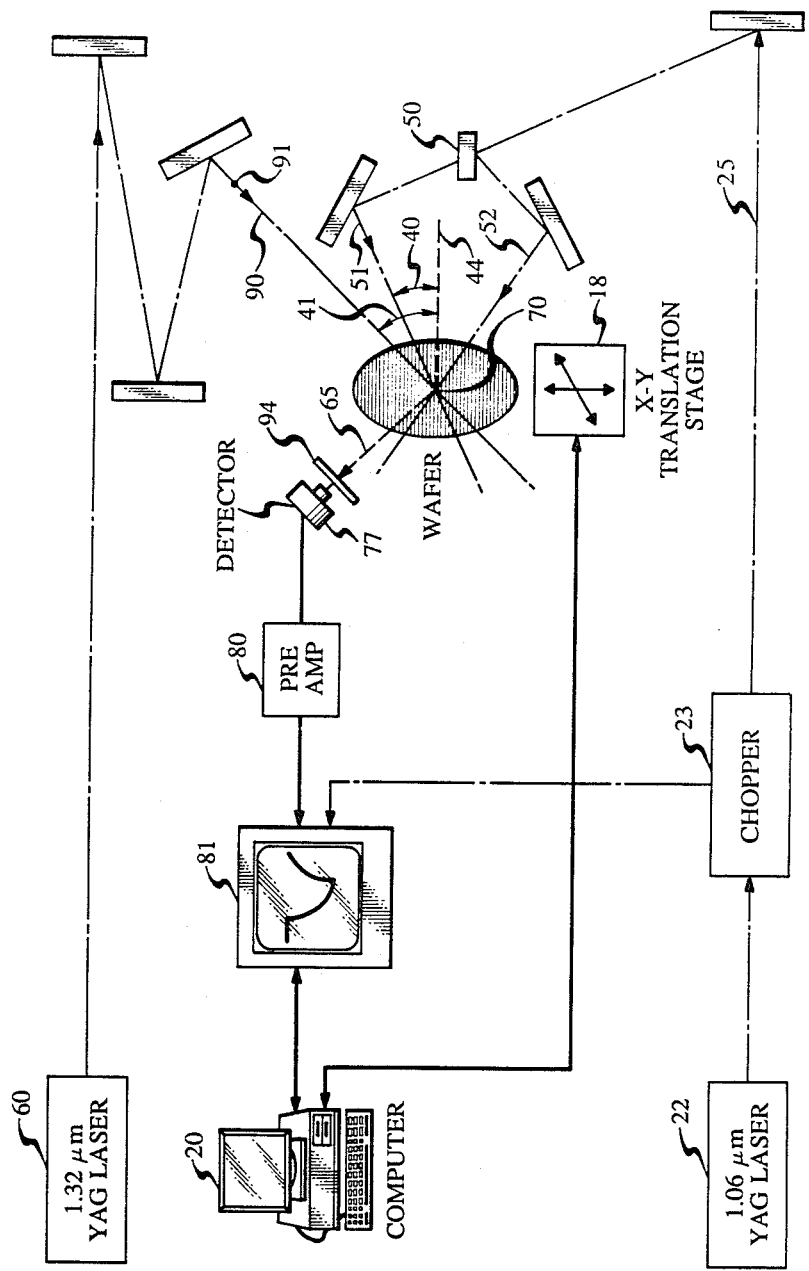

Various configurations are possible for inducing and monitoring refractive index change. Typically, the area illuminated by monitoring the beam should be comparable to or smaller than the area illuminated by the inducing beam. If this criterion is not satisfied, edge effects and optical non-uniformities in the inducing beam cause inaccuracies. A portion of the monitoring beam, if a grating is induced, is diffracted into a detector. This detector either has a limited detection area, e.g., a photodiode or is a large area, e.g., multiple element detector such as a vidicon. In the former case, the wafer is translated relative to the detection of the inducing beam and the monitoring beam to probe various regions of the wafer. In the latter case, the individual detection elements measure simultaneously differing regions of the wafer. For monitoring a uniform refractive index change focused inducing and monitoring beams are employed with a single element detector and associated phase sensitive optics as described in Collier, supra, Suyu, supra and Glass, supra. In this situation spatial information is obtained by moving the wafer relative to the beams and detector. Although monitoring of the change in refractive index has been discussed in terms of monitoring phase change or diffraction change, the phenomenon monitored is not critical. For example, it is possible to monitor gain or polarization change. The magnitude of the different phenomenon relating to refractive index varies and typically the one most easily measured is monitored. FIG. 1 shows typical configurations for a single element detector and FIG. 4 shows a corresponding typical configuration for a multiple element detector such as a vidicon.

For any of the described measurements utilizing a single element detector, spatial resolution is essentially the size of the monitoring beam. When a large area detector is employed with large area beams the resolution is essentially the larger of (1) the resolution of the optical system and (2) the resolution of the detector. For the induced grating embodiment, it is desirable that the grating period be smaller, e.g., at least 5 times smaller, than the monitoring beam diameter. (If the monitoring beam is not round, its diameter is that of a circle having the same area as that of the beam.) The rate of decay of the induced refractive index change after termination of the inducing radiation yields an accurate measure of resistivity. The exponential decay rate of the refractive index as described in reference 2 is directly related to the product of the resistivity and dielectric constant. Both the measurement itself and the conversion to electrical characteristics is easily automated utilizing conventional electronic signal processing equipment and is easily adapted to a device fabrication environment. Measurement of absorption characteristics as related to trap concentration and of photoconductivity is also possible as previously described.

The time required for making the measurement depends on the spatial area and the number of detections required to cover this area. If a vidicon is employed, substantially less time is needed. For typical single element detectors and typical wafer sizes e.g., 2 inches in diameter, periods of approximately ½ hour to 2 hours is required to inspect the entire wafer. The speed at which the inducing beam is terminated determines the smallest detectable resistivity. The termination speed is linearly related to the minimum resistivity with a termination speed of approximately 1 μsec required to detect a resistivity of approximately $10^6$ ohm-cm or greater.

The inducing light source should be chosen so that it is absorbed by the dopant or other deep traps that produce the semi-insulating wafer qualities. Typically, absorption characteristics of impurities in semiconductors is extensively documented. (See, e.g., *Optical Processes in Semiconductors*, I. Pankove, Dover Publications, Inc., New York (1975), pp. 62–67.) The absorption characteristics of each dopant depend not only on the dopant but also on the electronic band structure of the host semiconductor material. However, this interaction and a suitable wavelength range for the inducing beam is easily determined by measuring the photoconductivity spectral response as described in Pankove, supra. The dopant absorption data is a convenient spectral starting point for this determination. The light should be chosen so that excessively strong absorption, i.e., absorption greater than 90% is avoided. Also, the incident light should be chosen so that at least 0.01 percent of the inducing radiation is absorbed. If less than 0.01 percent of the light is absorbed, generally the resulting refractive index change is undesirably small and excessive measurement inaccuracies are encountered. Semi-insulating wafers in the context of this invention include a semiconductor body having a semi-insulating layer formed on it. Since these layers are typically quite thin, the wavelength of the inducing light should be carefully chosen to satisfy the above-described absorption criterion. For extremely thin layers it is possibly advantageous to monitor absorption change rather than refractive index change upon terminating the inducing beam. See, T. E. VanEck, L. M. Walpita, W. S. C. Chang and H. H. Wieder, *Applied Physics Letters*, 48, 451 (1986) and D. A. B. Miller, D. S. Chemla, D. J. Eilenberger, P. W. Smith, A. C. Gossard, W. Wiegman, *Applied Physics Letters*, 42, 925 (1983) for a description of the detection of an absorption change.

Typically, for materials such as III–V semiconductor materials refractive index changes of at least $10^{-6}$ are desirably produced. For useful dopant concentrations typically in the range $10^{15}$ cm$^{-3}$ to $10^{18}$ cm$^{-3}$ absorbed inducing radiation intensities in the range 0.1 watts/cm$^2$ to 10 watts/cm$^2$ generally allow reliable measurement.

The following examples are illustrative of the invention.

Example 1

The two-inch diameter semi-insulating gallium arsenide wafer having its major surface normal to a <001> direction was polished on both sides utilizing a conventional bromine methanol etch. This water had a thickness of approximately 20 mills, had a resistivity of approximately $10^8$ ohm-cm, had a trap density of approximately $3 \times 10^{15}$ cm$^{-3}$, and had an absorption coefficient of approximately 0.6 cm$^{-1}$ at a wavelength of 1.06 micrometers.

The wafers was placed on the sample holder, 18, of the apparatus shown in FIG. 1 with a <110> direction horizontal and with the perpendicular <110> direction in the plane of the wafer at an angle of 30 degrees to the vertical. This sample holder had an x-y translation stage that was controlled by computer, 20. The YAG laser, 22 (1.06 $\mu$m) was utilized as the inducing beam source. This laser was chopped at 23 by focussing the laser on the chopper and operating the chopper at 150 Hz. With this procedure a rise time and termination time of 10 microseconds for a pulse approximately 30 milliseconds in duration was obtained. The resulting pulses, 25, were split at beam splitter, 50, and combined at 70 to produce an interference pattern that, in turn, produces a diffraction grating in the wafer. This diffraction grating was sinusoidal in shape with a period of approximately 1.3 $\mu$m. (The angle between split beam, 51, and split beam, 52 was approximately fifty degrees.) The intensity in each of the intersecting beams was approximately 10 milliwatts per square millimeter, and the area of interaction of the beam at the wafer surface was approximately two millimeters in diameter.

A monitoring beam was obtained utilizing a 1.32 millimeter YAG laser, 60. The beam from this laser was made incident on the wafer at 70 so that it formed a specific angle relative to the two intersecting beams. To satisfy the Bragg condition and thus to allow diffraction from the grating, the angle 41 relative to angle 40 was adjusted to satisfy a specific condition. (Dotted line 44 is the bisection of the angle between beams 51 and 52.) The condition to be satisfied is that the ratio between the sine of angle 41 to the sine of angle 40 is the ratio of the wavelengths of the lasers, i.e., 1.32 $\mu$m, to the wavelength 1.06 $\mu$m. The intensity of the monitoring beam was approximately five milliwatts per square centimeter and impacted approximately a 2 millimeter diameter region that coincides with the area illuminated by the coincident beams, 51 and 52. The detector, 77, an indium gallium arsenide PIN detector with a detection region of two millimeters, was positioned to observe the light, 65, diffracted from the induced diffraction grating. (This light passed through filter 94 to remove any scattered light of 1.06 $\mu$m wavelength.)

Figure 3:
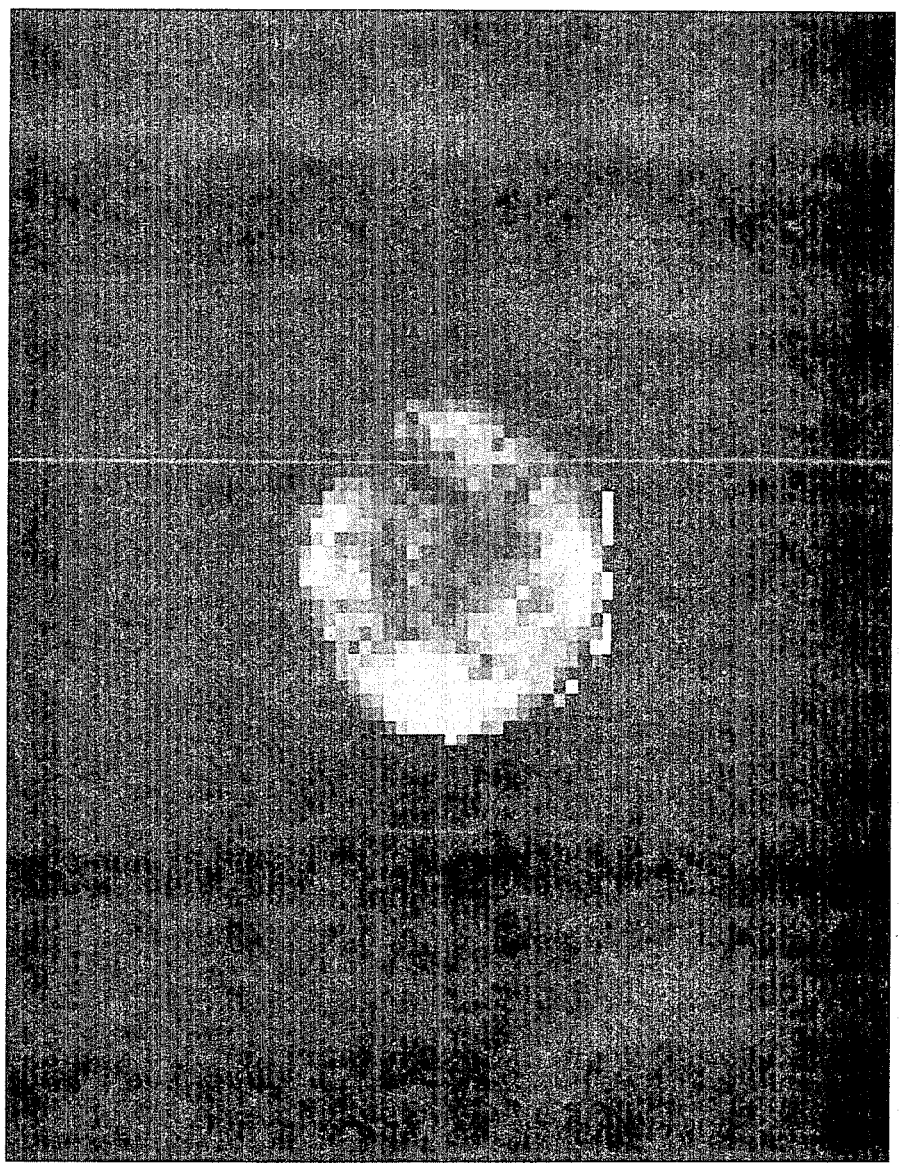
FIG. 3 is illustrative of measurements made in conjunction with the invention.

The signal from the detector is amplified by a factor of approximately $10^6$ and fed into the multichannel analyzer, 81. For each chopped pulse a resulting time varying electrical signal is fed into the multichannel analyzer that corresponds to the decay of diffracted light. Approximately three hundred such signals are measured and stored in the multichannel analyzer and the average of these curves is fed to the computer, 20. Computer 20 then takes the logarithm of the curve yielding a straight line whose slope is proportional to the resistivity of the wafer at point, 70. The x-y translation stage was then moved a distance of one and one-half millimeter and the procedure repeated. The stage was translated and the procedure repeated so that the wafer was mapped in a checkerboard pattern with each square of this pattern having a side of approximately one and one-half millimeters in length. The computer, 20, then generated a grey scale pattern corresponding to the spatial distribution of resistivity in the wafer as shown in FIG. 3. The brightest spot corresponded to a resistivity of approximately $21 \times 10^7$ ohm-cm and the dimmest spot corresponded to a resistivity of $9 \times 10^7$ ohm-cm.

Example 2

The procedure of Example 1 was followed except a wafer obtained from a different source was employed. The measured resistivity in this wafer varied from between $1 \times 10^8$ ohm-cm to $1.5 \times 10^8$ ohm-cm.

Example 3

The procedure of Example 1 was followed except a lens with a 50 centimeter focal length was positioned at a point, 91, a distance of 50 centimeters from point 70. This focussed reading beam, 90, at point 70 to a spot size of 250 $\mu$m. This procedure allowed the production of a checkerboard resistivity map with a finer scale than that obtained in Example 1.

Example 4

The procedure of Example 1 was followed except the averaging was done only over the time period which the inducing laser was on. This average information was fed into the computer which produced a map of absorption coefficient as a function of position corresponding to the map of resistivity shown in FIG. 3. In this spatial absorption map the variation in coefficient was plus or minus 25 percent from the average value.

What is claimed is:

1. A process for preparing a body comprising semi-insulating material, said process comprising the steps of (1) fabricating said semi-insulating body, (2) inducing with electromagnetic radiation a first refractive index profile in said material that differs from the unilluminated refractive index profile of said material, (3) changing the intensity of said electromagnetic radiation to cause a change in said first refractive index profile, (4) monitoring said change with electromagnetic radiation, (5) determining from the result of said monitoring the suitability of said body, and (6) employing said body based on said determination.

2. The process of claim 1 wherein said body comprises a material having a zinc blende crystal structure.

3. The process of claim 1 wherein said body comprises gallium arsenide.

4. The process of claim 1 wherein said first refractive index profile comprises a diffraction grating.

5. The process of claim 1 wherein said electromagnetic radiation comprises laser light.

6. The process of claim 1 wherein said change in intensity comprises a termination of said inducing electromagnetic radiation.

7. The process of claim 3 where said body comprises doped gallium arsenide.

8. The process of claim 4 wherein said electromagnetic radiation comprises laser light.

9. The process of claim 8 wherein said change in intensity comprises a termination of said inducing electromagnetic radiation.

10. A process for fabricating a plurality of devices comprising the steps of (1) preparing a wafer comprising a semi-insulating material, (2) inducing with electomagnetic radiation a first refractive index profile in a region of said wafer that differs from the unilluminated refractive index profile of said material, (3) changing the intensity of said electromagnetic radiation to cause a change in said refractive index profile, (4) monitoring said change with electromagnetic radiation, (5) determining from the result of said monitoring the suitably of said wafer, and (6) completing said plurality of devices on said suitable wafer.

11. The process of claim 10 wherein said body comprises a material having a zinc blende crystal structure.

12. The process of claim 10 wherein said body comprises GaAs.

13. The process of claim 10 wherein said first refractive index profile comprises a diffraction grating.

14. The process of claim 10 wherein said electromagnetic radiation comprises laser light.

15. The process of claim 10 wherein said change in intensity comprises a termination of said inducing electromagnetic radiation.

16. The process of claim 10 wherein said wafer is representative of a plurality of wafers and said devices on said wafers are completed based on said determination.

17. The process of claim 12 wherein said body comprises doped gallium arsenide.

18. The process of claim 14 wherein said electromagnetic radiation comprises laser light.

19. The process of claim 18 wherein said change in intensity comprises a termination of said inducing electromagnetic radiation.

20. A process for preparing a body comprising semi-insulating material, said process comprising the steps of (1) fabricating said body, (2) inducing with electromagnetic radiation an absorption that differs from the unilluminated absorption of said material, (3) changing the intensity of said electromagnetic radiation to cause a change in said absorption, (4) monitoring said change with electromagnetic radiation, (5) determining from the result of said monitoring the suitability of said boedy, and (6) employing said body based on said determination.

21. The process of claim 20 wherein said body comprises a semi-insulating layer formed on a wafer.

* * * * *

UNITED STATES PATENT AND TRADEMARK OFFICE
CERTIFICATE OF CORRECTION

PATENT NO. : 4,777,146

DATED : 10/11/88

INVENTOR(S) : Richard B. Bylsma and Alastair M. Glass

It is certified that error appears in the above-identified patent and that said Letters Patent is hereby corrected as shown below:

Column 5 line 35 "<110>" should read --<1$\bar{1}$0>--.

In the claims, column 8 line 30 "boedy" should read --body--.

Signed and Sealed this

Twenty-ninth Day of August, 1989

*Attest:*

DONALD J. QUIGG

*Attesting Officer*     Commissioner of Patents and Trademarks